(12) United States Patent
Semenuk (10) Patent No.: US 10,940,711 B2
(45) Date of Patent: Mar. 9, 2021

(54) BANDAGE WITH AN INSERTABLE MEDICAL DATA CARD

(71) Applicant: S.A.L. Mine, Inc., Lighthouse Point, FL (US)

(72) Inventor: Margaret M Semenuk, Lighthouse Point, FL (US)

(73) Assignee: S.A.L. MINE, INC., Lighthouse Point, FL (US)

( * ) Notice: Subject to any disclaimer, the term of this patent is extended or adjusted under 35 U.S.C. 154(b) by 666 days.

(21) Appl. No.: 15/400,130

(22) Filed: Jan. 6, 2017

(65) Prior Publication Data
US 2018/0194153 A1   Jul. 12, 2018

(51) Int. Cl.
*A61F 13/00* (2006.01)
*B42D 25/22* (2014.01)
(Continued)

(52) U.S. Cl.
CPC ........ *B42D 25/22* (2014.10); *A61F 13/00051* (2013.01); *A61F 13/00059* (2013.01);
(Continued)

(58) Field of Classification Search
CPC ........ B42D 15/00; B42D 25/22; B42D 25/28; B42D 25/00; B42D 15/045; B42D 15/0086; A61F 13/00051; A61F 13/00059; A61F 13/00; A61F 2013/00089; A61F 2013/00182; A61F 2013/00153; A61F 2013/00106; A61F 2013/00361;
(Continued)

(56) References Cited

U.S. PATENT DOCUMENTS 3,921,318 A   11/1975   Calavetta
3,958,690 A   5/1976   Gee, Sr.
(Continued)

FOREIGN PATENT DOCUMENTS

WO   WO 9844846 A1   10/1998
WO   WO 2008157232 A1   12/2008

OTHER PUBLICATIONS

"Absolutely Free Printable Medical ID Cards," MedIDs.com, medids.com, accessed: Nov. 2016. http://web.archive.org/web/20041204073107/http://medids.com/freeid.php.
(Continued)

*Primary Examiner* — Victoria J Hicks
(74) *Attorney, Agent, or Firm* — Robert C. Kain (57) ABSTRACT

A bandage with an insertable medical data card consisting of a bandage with a central pocket, a slit for accessing the pocket, a flap for sealing the pocket, and a transparent faceplate on the pocket. The medical data card contains pertinent medical data of a user adapted to be inserted into the pocket of the bandage and the bandage worn upon the body of the user. The bandage is changeable every three to four days and the medical data card can be transferred from one bandage to another. The system provides a wearable medical data card which instantly informs first responders and medical caregivers of the user's pertinent medical information, saving precious time while life saving measures based on the pertinent medical information gleaned from the medical data card are being implemented.

10 Claims, 8 Drawing Sheets

(51) Int. Cl.
*B42D 25/28* (2014.01)
*B42D 15/00* (2006.01)
*B42F 7/02* (2006.01)

(52) U.S. Cl.
CPC ..... *B42D 15/0006* (2013.01); *B42D 15/0086* (2013.01); *B42D 25/28* (2014.10); *B42F 7/025* (2013.01); *A61F 2013/00182* (2013.01)

(58) Field of Classification Search
CPC .... A61F 2013/00544; A61F 2013/0057; A61F 2013/00655; A61F 13/02; A61F 2013/00846; A61F 2013/00795; A61F 2013/00365; A61F 2013/00553
USPC .......................................................... 40/633
See application file for complete search history.

(56) References Cited

U.S. PATENT DOCUMENTS

| | | | |
|---|---|---|---|
| 4,236,332 A * | 12/1980 | Domo | G09F 3/00 283/76 |
| 4,896,027 A | 1/1990 | Drexler | |
| 4,984,683 A | 1/1991 | Eller | |
| 5,161,826 A | 11/1992 | Van Giensen et al. | |
| 5,171,039 A | 12/1992 | Dusek | |
| 5,197,763 A | 3/1993 | Whalen | |
| 6,050,605 A | 4/2000 | Mikelionis et al. | |
| 6,223,559 B1 | 5/2001 | Coleman | |
| 6,455,752 B1 | 9/2002 | Vesey | |
| 6,944,767 B1 | 9/2005 | Judson | |
| 7,005,170 B1 | 2/2006 | Simpson et al. | |
| 7,205,448 B2 | 4/2007 | Levin | |
| 7,257,967 B2 | 8/2007 | Rheinstein | |
| 8,132,711 B2 * | 3/2012 | Clark | B65D 27/14 229/68.1 |
| 8,959,815 B2 | 2/2015 | Hopman et al. | |
| 9,138,144 B2 | 9/2015 | Geva | |
| 2003/0059751 A1 | 3/2003 | Welles | |
| 2004/0158186 A1 | 8/2004 | Hall | |
| 2004/0199408 A1 | 10/2004 | Johnson | |
| 2005/0110268 A1 | 5/2005 | Schone | |
| 2005/0133554 A1 | 6/2005 | Maupin | |
| 2008/0319798 A1 | 12/2008 | Kelley | |
| 2009/0049722 A1 | 2/2009 | Chan | |
| 2009/0101721 A1 | 4/2009 | Hawthorne et al. | |
| 2013/0054266 A1 * | 2/2013 | Oakley | G16H 10/65 705/3 |

OTHER PUBLICATIONS

"Medical information ID Card identification card for medical Safety," Safety Identification Printing, safetyidentificationproducts.com, 2003. http://www.safetyidentificationp.

45 CFR 160.103—"Definitions, US Law, Legal Information Institute", https://www.law.cornell.edu/cfr/text/45/160.103 (12 pages).

* cited by examiner

FIG.1

Name
Blood Type
Allergies
Medications
Conditions
Hospital-Doctor
Person to be Notified
Faith/Religion

SS#
DOB

BANDAGE WITH AN INSERTABLE MEDICAL DATA CARD

This is a regular patent application pursuant to 35 U.S.C. § 11 (a) titled "Bandage With an Insertable Medical Data Card."

The present invention is a bandage with an insertable medical data card so that the medical data card is wearable and further, a method of using a two-bandage system with a re-insertable medical data card.

BACKGROUND OF THE INVENTION

Wearable emergency medical alerts are known. Medical alerts are available as a bracelet or necklace and provide emergency care workers with immediate notice of a serious condition or life threatening allergy. However, the medical alert jewelry contains a very limited amount of information, typically, only the name of the serious condition or allergy. It does not provide the patients name, or information, doctor name(s) or current medications. All of this information is critical to a patient's care during emergency treatment.

Bandages are known. Bandages are used to cover wounds on the body. Bandages protect the wounds from the elements, including bacteria, while the wound is healing. Some bandages provide waterproof protection. Some bandages are not readily removable in water.

Medical information cards are known. U.S. Pat. No. 8,959,815 to Hopman et al. discloses a device for recording medical information for an injured person made of a sheet of a flexible film including an imprinted form suggesting desired patient information and including a writing surface on which to record patient information and a fastening layer of an adhesive material associated with and arranged with respect to the sheet of flexible film so as to be capable of adhering the sheet of flexible film to an injured person.

U.S. Pat. No. 5,197,763 to Whalen discloses a kit form wherein individuals can create their own emergency medical data card, with a blank form that includes indicia having individualized, personalized information, such as name, address, and a series of medical indicia information that includes lines from each word so that an individual can fill in the particular information required.

U.S. Pat. No. 6,944,767 to Judson discloses ensuring the security of data from a medical test that includes providing the patient with a medical data card issued by a secure information provider, and having a unique patient identification number (PID), a public key encryption private key, and public key encryption public key. U.S. Pat. No. 4,896,027 to Drexler discloses a compact auxiliary data record storing at least one quarter megabyte of data in card size and detachably adherable to a support surface. Drexler is a data card for storing computer data.

U.S. Pat. No. 9,138,144 to Geva discloses an adhesive bandage computer system memory that stores patient data, drug data and emergency information and also can take vitals. The bandage system communicates with a PDA.

U.S. Patent Publication No. 2008/0319798 to Kelley discloses creating an online medical information record which contains the individual's stored personal medical information, providing the individual with a physical credit card sized card. U.S. Pat. No. 6,223,559 to Coleman discloses a medical identification charm bracelet wherein each charm attachment includes a housing having a die cut panel and a visible display of a different specific medical condition of the individual.

U.S. Pat. No. 7,205,449 to Levin discloses an adhesive bandage having markings or indicia providing wound care instructions. The bandage can be placed over a wound with a clear indication printed on the bandage about what treatment the wound or patient should receive. U.S. Pat. No. 3,921,318 to Calvetta discloses a medical history card. The card has a jacket printed with identification information taken from a form and critical medical information.

U.S. Pat. No. 5,161,826 to Van Giesen et al. discloses a medical information card that identifies any metallic elements that have been put inside the persons body. U.S. Patent Application Publication to Hall discloses a indicia bearing adhesive bandage used to cover the site of a vaccination injection. U.S. Pat. No. 3,958,690 to Gee, Sr. discloses a medical information card inserted into a transparent sleeve. Free printable medical ID cards are known. For example, they are available on www.MedIDs.com, medids.com. The user creates a free personal medical ID wallet card on his computer keyboard by completing the form and printing out the final card on his printer. There are many known medical data cards and alerts, however, they are not easy to update and not wearable with the ability to contain all the necessary information.

OBJECTS OF THE INVENTION

It is an object of the present invention to provide a wearable medical data card that is easy to update when pertinent medical data or contact information is changed. The medical data card will be immediately identifiable to first responders and provide the responders with all the information they need to treat the patient without causing harm due to unknown conditions, procedures or medications. The information will immediately identify the patient's hospital and doctors of choice. The information will be immediately available to the hospital and treating doctor before the patients arrival at the hospital. The information will also identify the emergency contact information for the patient, so that person(s) may be contacted immediately by first responders.

It is a further object of the invention to provide a bandage that contains a pocket for holding a medical data card. The pocket on the bandage is easily accessible through a slit in the pocket through which the medical data card can be inserted. The pocket is then sealable by covering the slit with a flap, which makes the pocket watertight to prevent the medical data card from being damaged by liquids. The medical data card is visible through a transparent faceplate of the pocket. The medical data card is removable from the pocket of the bandage and the bandage replaceable with a new bandage as needed.

SUMMARY OF THE INVENTION

The present invention generally relates to a bandage with an insertable medical data card consisting of a bandage with a central pocket, a slit for accessing the pocket, a flap for sealing the pocket, and a transparent faceplate on the pocket. The medical data card contains pertinent medical data of a user adapted to be inserted into the pocket of the bandage and the bandage worn upon the body of the user. The bandage is changeable every three to four days and the medical data card can be transferred from the pocket of one bandage to another. The system provides a wearable medical data card.

In one embodiment, the bandage has an insertable medical data card and the bandage includes a central pocket formed from a body of the bandage and a transparent faceplate on a outward facing surface of the bandage. The bandage includes a slit for accessing the pocket, a flap laying over the slit with an adhesive layer on the underside of the flap. The bandage includes an adhesive layer on the back of the bandage for adhering the bandage to a user. The medical data card contains pertinent medical data of the user. The user adds their pertinent medical data to the card by adhering at least one removable adhesive backed label onto the card. The medical data card is adapted to be inserted into the pocket of the bandage through the slit and the flap seals the slit closed with the pertinent medical data viewable through the transparent faceplate when the bandage is worn upon the body of the user.

In another embodiment, the user adds their pertinent medical data to the card by the user inputting the information into a computer and printing the complete medical data card. Then the medical data card is adapted to be inserted into the pocket of the bandage through the slit and the flap seals the slit closed with the pertinent medical data viewable through the transparent faceplate when the bandage is worn upon the body of the user.

BRIEF DESCRIPTION OF THE DRAWINGS

Further objects and advantages of the present invention can be found in the detailed description of the preferred embodiments when taken in conjunction with the accompanying drawings in which.

DETAILED DESCRIPTION OF THE PREFERRED EMBODIMENTS

Figure 5:
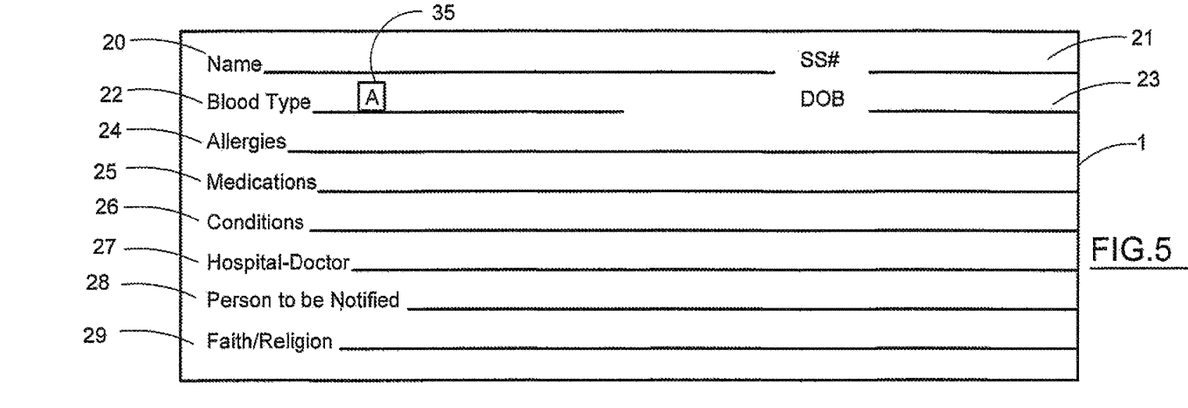
FIG. 5 is a front view of a medical data card.
Figure 6:
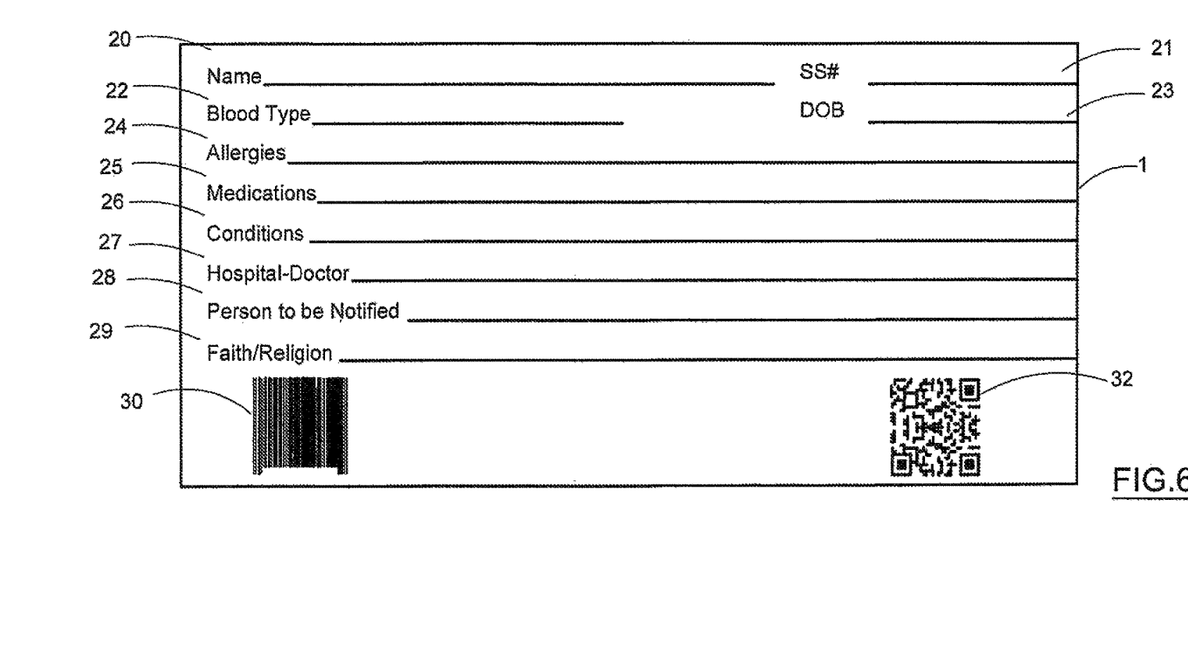
FIG. 6 is a front view of a medical data card created by a computer.

The bandage has an insertable medical data card which consists of a card with pertinent medical data of a user adapted to be inserted into the bandage with a transparent face. The bandage is worn upon the body of the user to alert medical officials and first responders in an emergency of the user's pertinent medical information. There are several embodiments for the wearable medical data card system. As shown in FIG. 5, in the first embodiment, the medical data card 1 is completed by the user adhering removable adhesive backed labels onto the card 1 and/or handwriting in additional information. The filled-in medical data card 1 (as shown in FIG. 5) is then inserted into a bandage 5. In the second embodiment, also shown in FIGS. 1 and 2, the medical data card 1 is completed by the user entering the required information into a questionnaire or form on a website. The completed form is then printed on a supplied medical data card 1 or is printed on a piece of paper or card stock. The computer-generated medical data card 1 (as shown in FIG. 6) is then inserted into a bandage 5.

Figure 1:
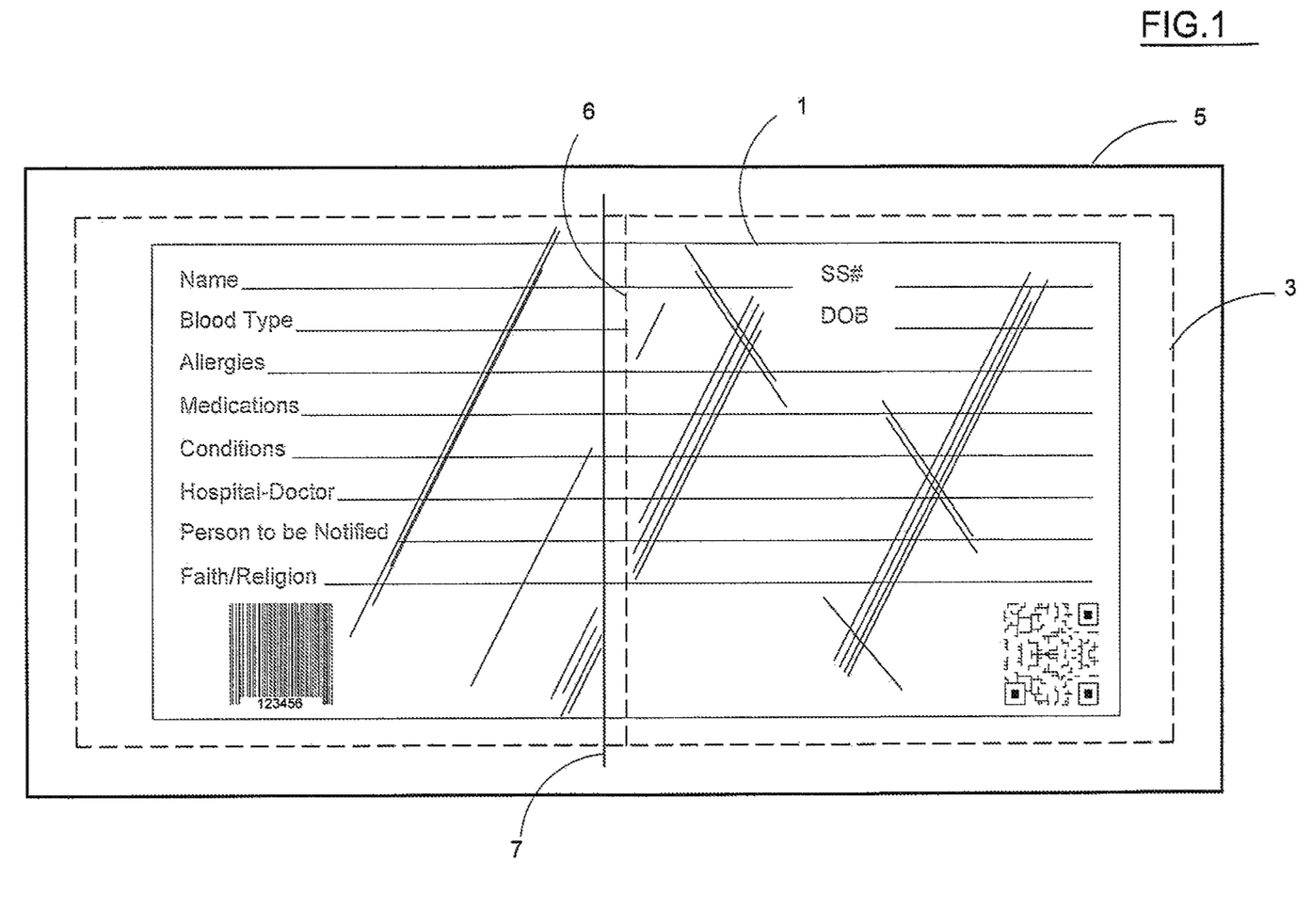
FIG. 1 is a front view of a bandage with a medical data card inserted in it with the slit in the middle of the bandage.
Figure 2:
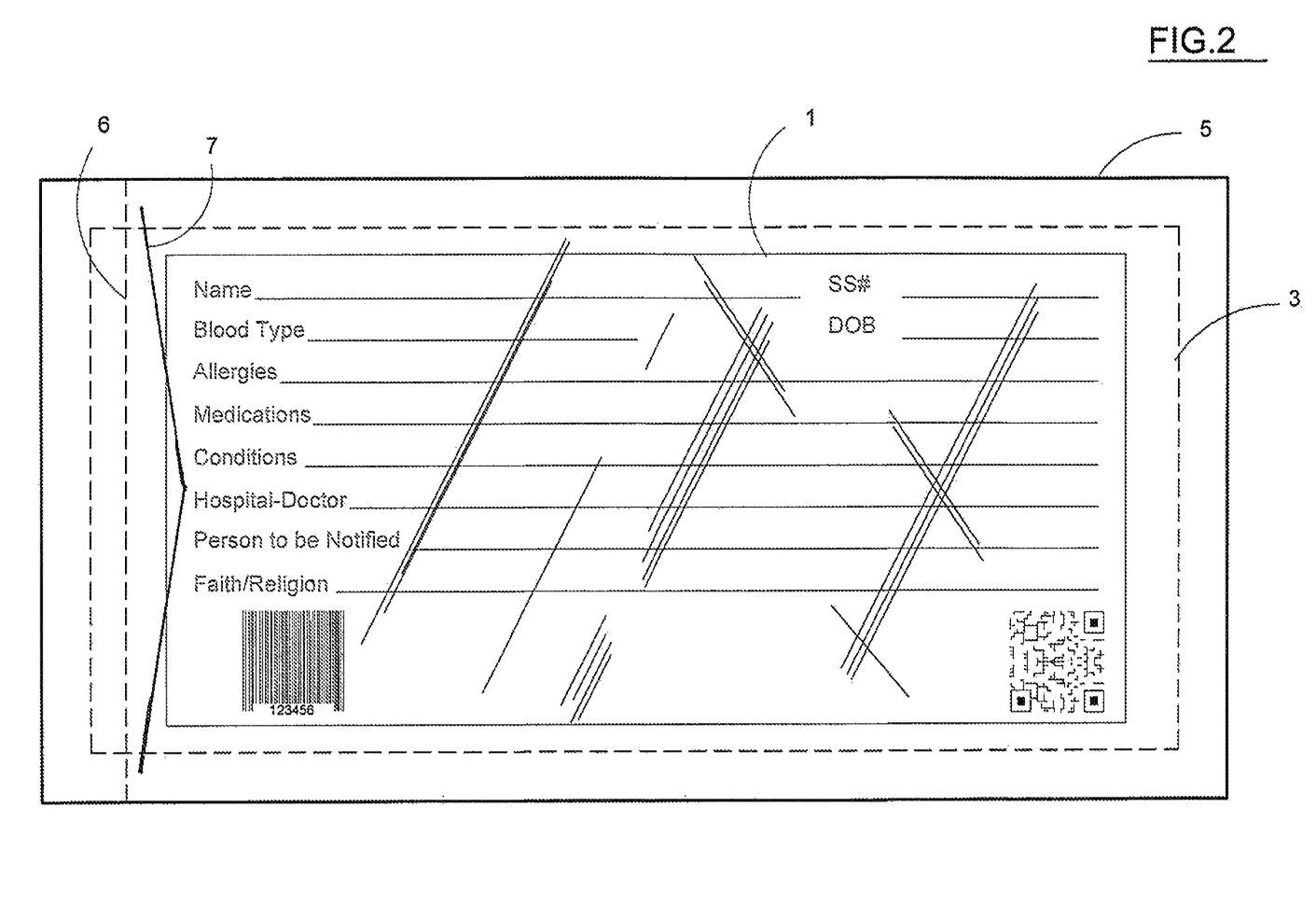
FIG. 2 is a front view of a bandage with a medical data card inserted in it with the slit on the side.
Figure 3A:
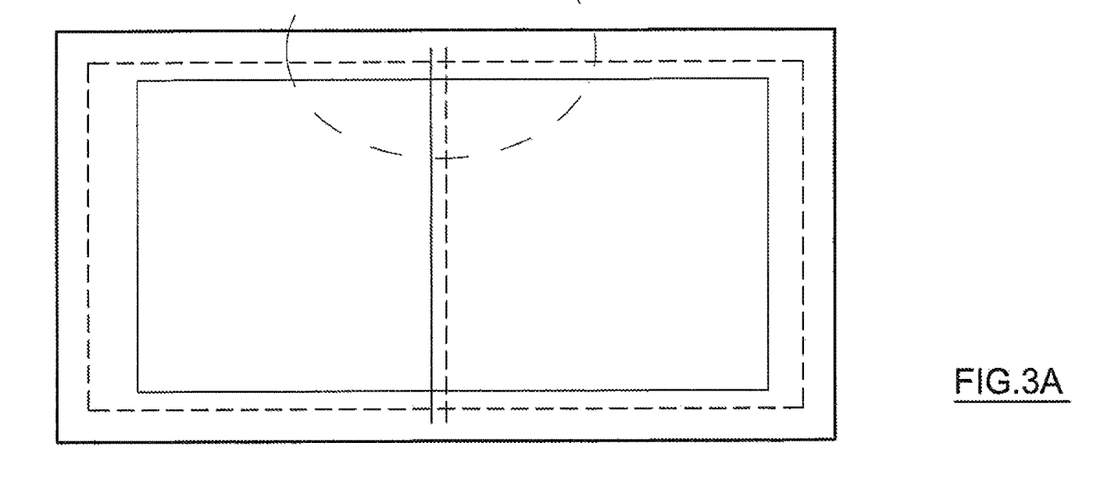
FIGS. 3A and 3B disclose a close up view of the opening and its flap closure in the bandage.

As shown in FIGS. 1 and 2, the medical data card 1 is placed within a bandage 5 by insertion of the medical data card 1 through a slit 6 in the bandage 5. A pocket 11 is formed by the body of the bandage 5 and the transparent faceplate 3 (see FIG. 3). The slit 6 opens into the pocket 11 so that the medical data card 1 can be inserted into the pocket 11. The slit 6, shown in dashed lines, is designed so that once the medical data card 1 is inserted, it can be sealed closed with flap 7, which forms a substantially watertight seal or nearly watertight seal. The slit 6 and flap 7 can be in the center of the bandage 5, as shown in FIG. 1 or near the edge of the bandage, as shown in FIG. 2. The slit 6 can be located anywhere on the periphery of the pocket 11 of the bandage 5. For example, the slit 6 may be on the sides, the top, or bottom edge of the pocket 11. The flap 7 can be various shapes, including but not limited to a straight flap as shown in FIG. 1, an envelope style or "v" shaped flap 7 as shown in FIG. 2, or a curved flap 7.

Figure 7:
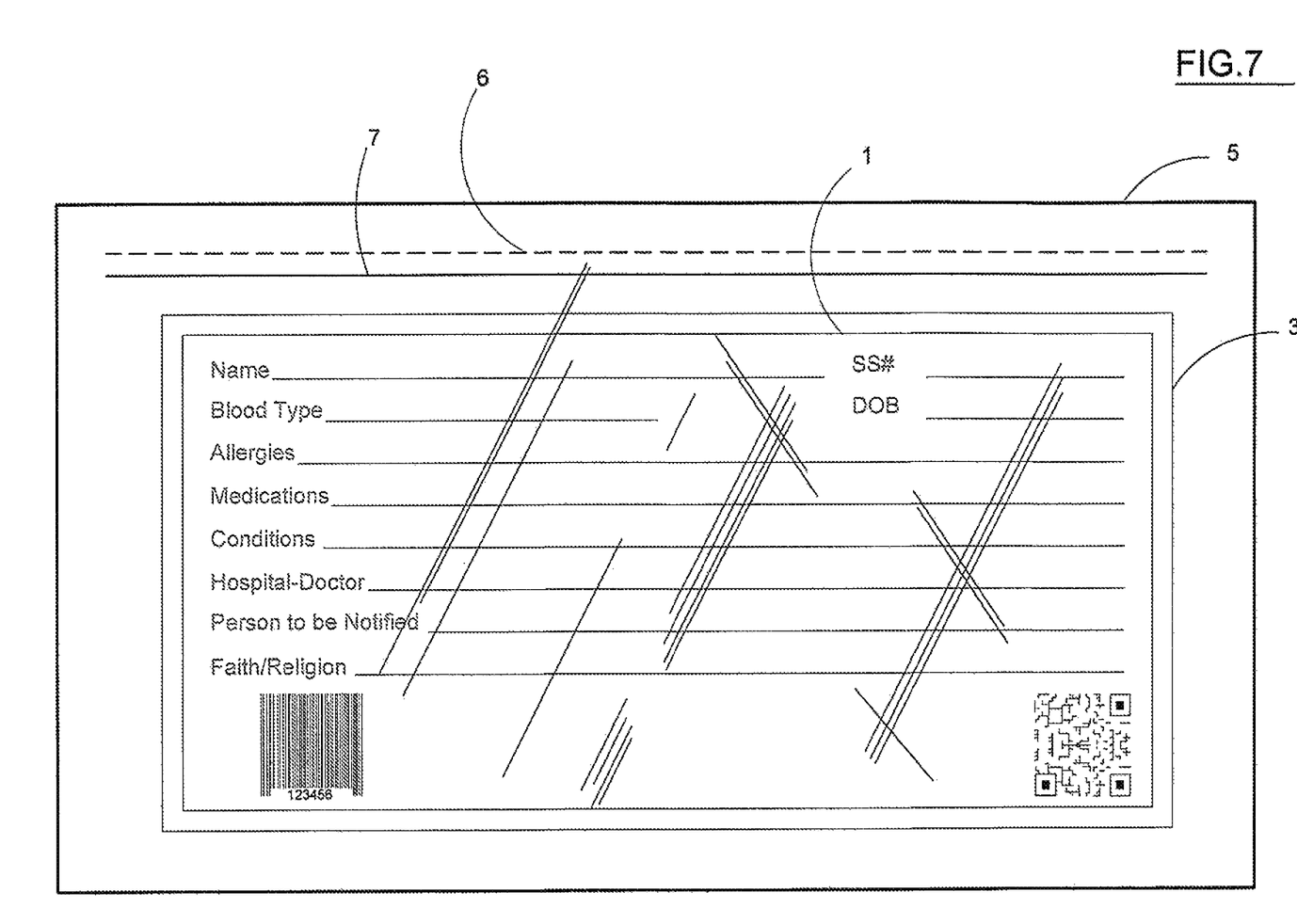
FIG. 7 is a front view of a bandage containing a medical data card viewable through the transparent window of the bandage with the slit on the top of the bandage.

FIG. 7 shows the bandage 5 with the slit 7 on the top of the bandage 5. This allows the medical data card 1 to be slipped into the pocket 11 of the bandage 5 and provides an unobstructed view of the information on the medical data card 1.

Figure 3B:
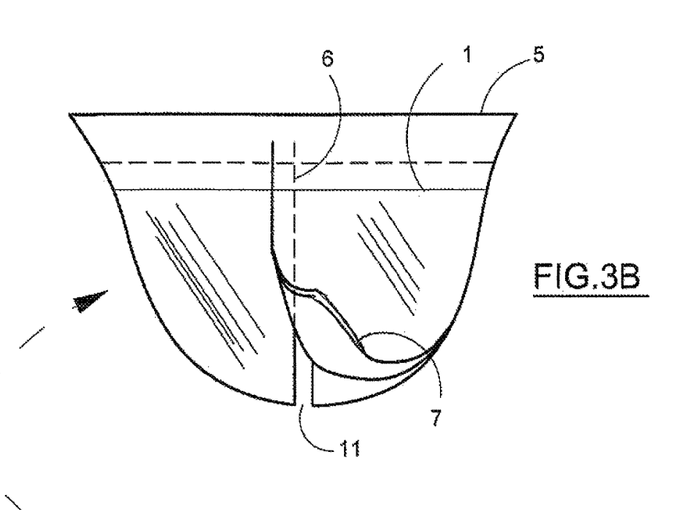

FIG. 3A is a partial view of the bandage and FIG. 3B is a close up view of the slit 6 in the bandage 5. The slit 6 is shown in dashed lines, because it is covered by a flap 7. Flap 7 is lifted to reveal pocket 11. After the medical data card 1 is inserted into pocket 1, flap 7 is sealed over the slit 6, so no water can enter and damage the medical data card 1. The medical data card 1 is preferably printed with ink that is impervious to damage from liquids. The flap 7 seals the slit 6 with an adhesive layer being on the underside of the flap 7, such that when the backing cover over the adhesive layer of the flap 7 is removed, the flap 7 is set over the slit 6 and seals the slit 6 closed. The adhesive used in flap 7 resists deteriorating or losing its adhesiveness in the presence of liquid.

Figure 4:
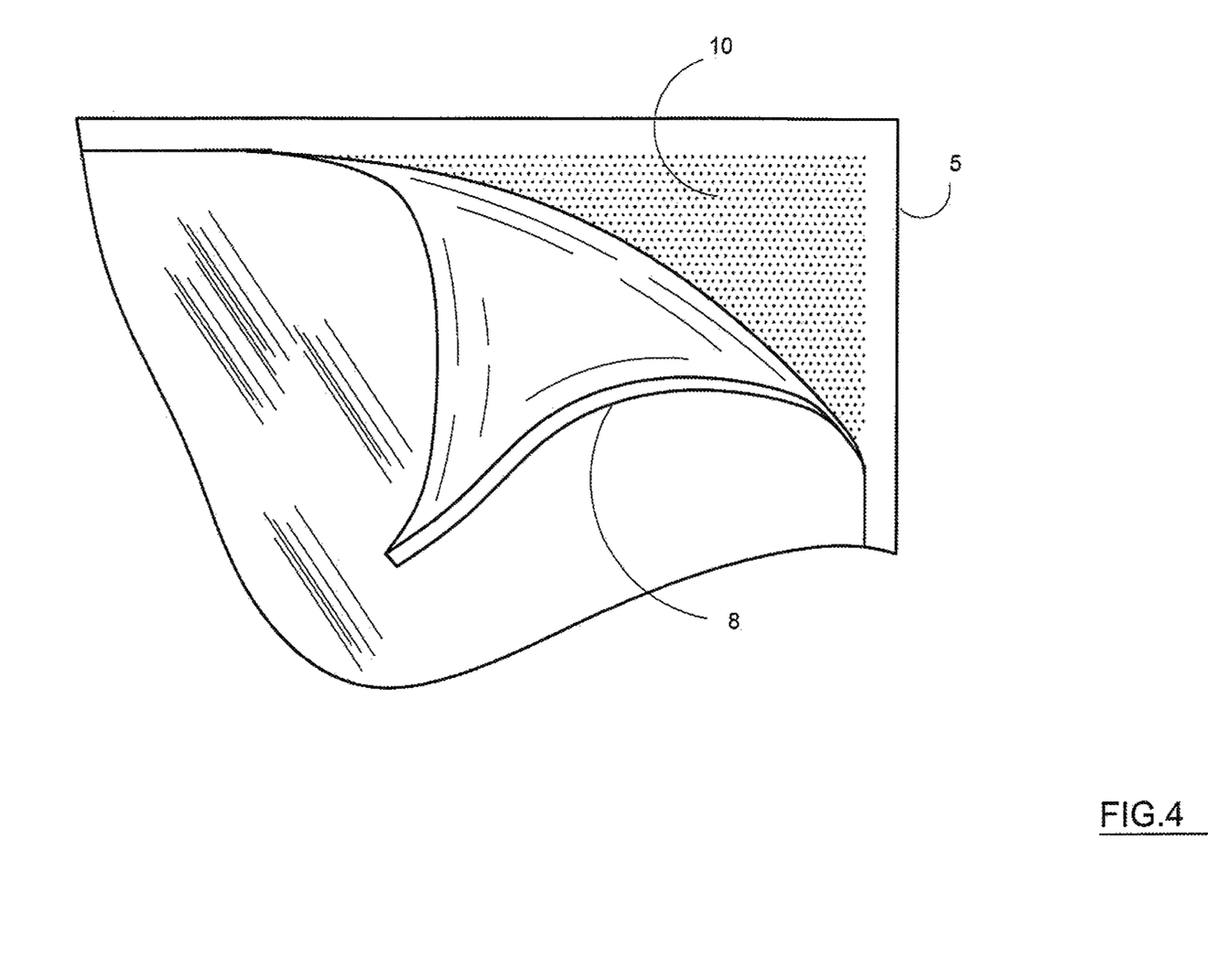
FIG. 4 is a partial view of the back of the bandage showing the adhesive and cover.

FIG. 4 shows a partial view of the backside of the bandage 5. The bandage 5 is preferably made of a plastic waterproof or water-resistant material. The bandage 5 can be made of any water-resistant material that is known. The bandage 5 is attachable to the body by an adhesive layer 10 on the underside of the bandage 5. A cover layer 8 covers the adhesive layer 10 and protects it until the user is ready to apply the bandage 5 to their body.

One embodiment of the present invention is ideal for people who are not computer savvy or do not have a computer or printer. A significant portion of the elder community, who are in need of a medical alert card and would greatly benefit from a medical alert card, do not use computers or prefer the option of not being required to use a computer.

As depicted in FIG. 5, the medical data card 1 is completed by the user adhering removable adhesive backed labels 35 or stickers onto the card and/or handwriting in additional information. The filled-in medical data card 1 is then inserted into a watertight pocket 11 of a bandage 5 (as shown in FIGS. 1 and 2).

The medical data card 1 carries critical medical data of the user and the card is inserted into a slit 6 or pocket on a bandage 5. The medical data card 1 is preferably 2.0"×3.5" in size, but can be any size that would accommodate the required information, remain legible and fit within the provided bandage. In preferred embodiments, the bandage 5 is substantially watertight. In one embodiment the bandage 5 is 2.5"×4.0," but the bandage 5 can be any size so long as it accommodates the medical data card 1.

As shown in FIG. 7, the bandage 5 carrying the medical data card 1 has a transparent faceplate 3 enabling any third party to view the data on the card 1 when the bandage 5 is worn on the body of the user.

Figure 8:
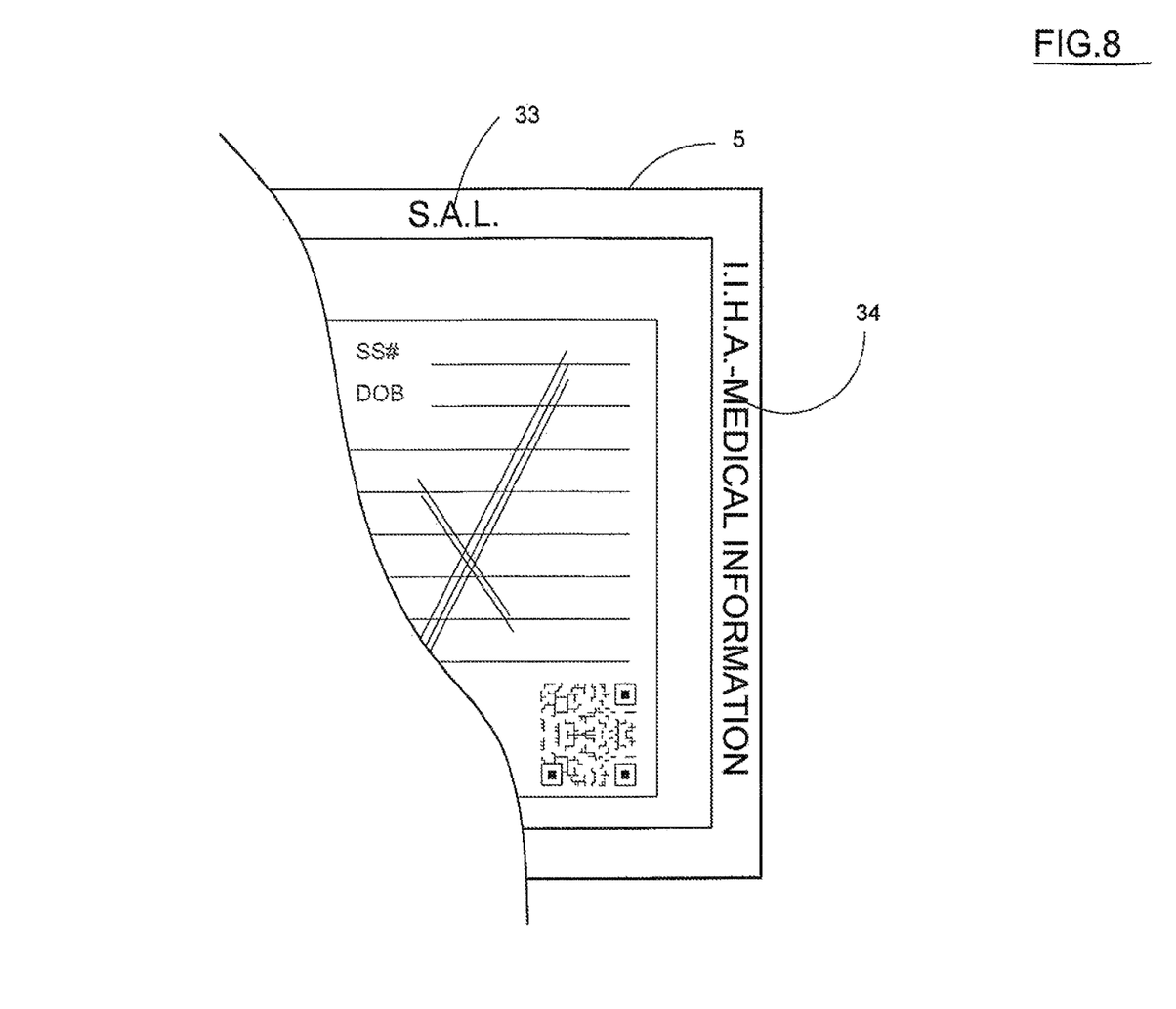
FIG. 8 is a partial view of the corner of the bandage showing emergency indications printed on the edges.

As shown in FIG. 8, all 4 borders of the bandage 5 can have "S.A.L." (for Save A Life-a reference to the manufacturer) printed on the borders to alert the paramedic or emergency room that it is the patient's medical and personal information. Any text can be printed on the bandage 5 to alert medical professionals that it contains emergency information.

In order to prepare the medical data card 1, as shown in FIG. 5, the user is given sheets with removable adhesive backed labels 35 or stickers. Some of the labels 35 are pre-printed with medical descriptions and/or letters and numbers. As shown in FIG. 5, the user removes the desired label 35 from the backing and sticks the label onto the medical data card 1 in the appropriate section. For example, the sheet will include labels for different blood types A, B, AB and O and the user peels off the correct label 35 listing his or her blood type and places that self adhering label strip onto the medical data card 1. As shown in FIG. 5, the user would put the desired blood type label 35 in the blank that calls for "blood type" 22. Different sheets are provided to the user for different ailments such as heart conditions, limb or extremity conditions, liver conditions, drug allergies, stent, etc.

As shown in FIGS. 5 and 6, the medical data card 1 will include a variety of pertinent information including, the user or patient's name 20, the user's social security number 21 or portions thereof (for example the last four numbers), the user's blood type 22 and the user's date of birth 23. The medical data card 1 will also include an area for attaching labels 35 or writing in: allergies 24, medications being taken 25, conditions or diseases 26, hospital(s) and doctor(s) of choice 27, person to be notified in the event of emergency 28, and faith/religion 29. The conditions or diseases 26 can be indicated with a universal coding system, such as CPT coding. CPT coding is the Current Procedural Terminology code set, published and maintained by the American Medical Association. CPT codes are used to describe tests, surgeries, evaluations, and any other medical procedure performed by a healthcare provider on a patient. A universal code set would be immediately recognizable by emergency workers and medical professionals. The information on the card is provided by way of example, it being understood that any relevant medical data can be included on the card 1. If the user wants, he/she can also include his/her faith/religion 29 on the medical data card. The faith/religion section 29 could include medical procedures that are not desired based upon faith of the user or it could include the name of a priest to be contacted.

As in the embodiment in FIG. 6, the medical data card 1 can also include a bar code 30 or a QR code 32, or an equivalent code. A one-dimensional (1-D) barcode 30 systematically represent data by varying the widths and spacings of parallel lines, and may be referred to as linear or one-dimensional. These include some of the traditional, or most well recognized barcode types such as the UPC and EAN code types. A QR Code 32 is a two-dimensional barcode that is readable by smartphones. It can encode over 4000 characters in a two dimensional barcode. QR Codes 32 may be used to display text to the user, to open a URL, save a contact to the address book or to compose text messages.

"QR Code" is a registered trademark of Denso Wave, Inc. The medical data card 1 could include either a bar code 30 or a QR code 32 to convey information electronically to the emergency workers, hospitals and doctors.

After the user has prepared the medical data card 1 with user supplied medical information, the user slips the prepared card 1 into the pocket of the first bandage 5 and places the bandage 5 on his or her body as a first adhered condition. The bandages are adopted to be placed on the skin of the user. Periodically, about every three to four days, the user removes the first bandage 5 and removes the card 1 from the pocket and inserts the medical data card 1 into a second, new replacement bandage 5 and applies the replacement bandage 5 to his or her body as a second adhered condition. This procedure is used for both the first and second embodiments where the medical data card 1 is prepared and put into the bandage 5.

In another embodiment, as shown in FIGS. 6 and 7, the user purchases bandages 5 that are designed to be nearly watertight with a slit 6 where the medical data card 1 is inserted. There is a flap 7 over the slit 6 so no water can enter into the compartment where the medical data card 1 is inserted.

As shown in FIG. 8, there are emergency medical data notices 33, 34 printed around the border of all 4 sides of the bandage 5. The emergency information can be the initials "S.A.L." 33 or any other emergency indicator 34. The emergency medical data notice 33, 34 could optionally be printed on the medical data card 1 borders instead of the bandage 5. When the emergency medical data notice 33, 34 is printed on the card 1, the information is seen through the clear transparent window 3 of the bandage 5. The emergency medical data notice 34 may indicate that the bandage contains medical information about the user including but not limited to "individually identifiable health information" or "IIHA." Individually identifiable health information is information that is a subset of health information, including demographic information collected from an individual, and (1) is created or received by a health care provider, health plan, employer, or health care clearinghouse; and (2) relates to the past, present, or future physical or mental health or condition of an individual; the provision of health care to an individual; or the past, present, or future payment for the provision of health care to an individual; and (i) that identifies the individual; or (ii) with respect to which there is a reasonable basis to believe the information can be used to identify the individual. See 45 CFR 160.103.

Figure 9:
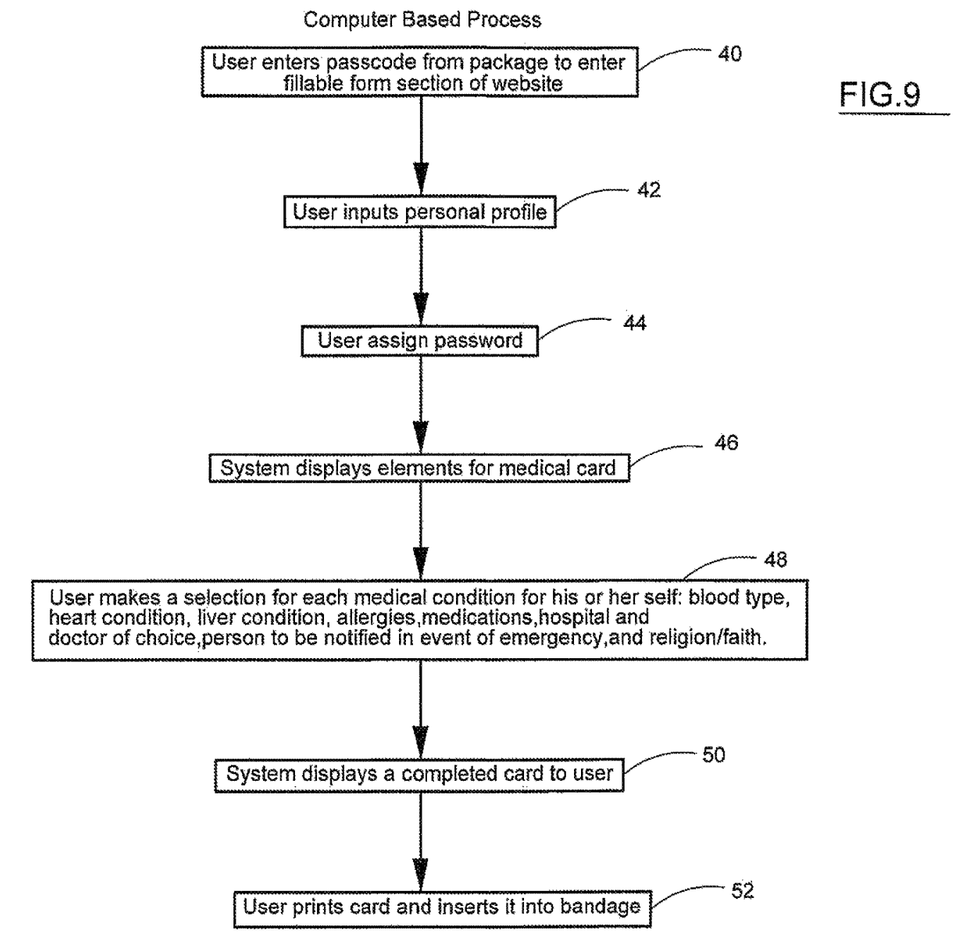
FIG. 9 is a flow chart identifying the computer process for creating the medical data card.

As shown in FIG. 9, in order to print the medical data card 1 for the bandage 5, the user must enter the required information into a website to produce the medical data card 1 by a computer based process. The purchaser or user is given a pass code with his purchase of a medical data card bandage kit to use to enter a designated website. At the designated website, in step 40, the user enters the passcode from the package to enter the portion of the website designated for the creation of the medical data card. In step 42, the user inputs their personal profile. In step 44, the user assigns a password to their profile. In step 46, the system will display the information needed for the medical card. In step 48, the user will answer questions about themselves and their medical history, conditions and medicine. In most cases, a window will come down for the user to pick which item answers that question. For example, the question can be "What is your blood type?" and the selections will be A, A Positive, A Negative, B, B Positive, B Negative. AB, O, O Negative. The user will select their blood type and the answer will fill that box. The user will continue until all the information is inserted onto the form, including blood type, date of birth, allergies, medications, conditions, hospital-doctor of choice, person to be notified in case of emergency, and religion/faith if desired.

In step 50, the system will display a completed card to the user. The user will then insert the blank card like form which was provided into his printer and print the information onto the card in step 52. There can be several cards per sheet. For example, there can be 10 cards per printing sheet. The card the customer just printed is than inserted into the bandage provided, also shown in step 52. Optionally, the user may be able to print the card on regular paper and cut the card out to fit in the pocket of the bandage. The bandage can be changed every 3 to 4 days and the card reinserted into the new bandage. The user may be prompted by reminder emails, or other communication, to update their medical data card information.

After the bandages provided in the original box are used, the user can then purchase refill bandages. Small S.A.L. charms are also attachable to a wrist watch or bracelet to alert everyone that the person has a medical data card on their body. The wearable medical data is ideal for any patient that has an emergency and is incapacitated. Patients with Alzheimer's can also benefit from wearing their medical and contact data, should they become disoriented and get lost.

The significant benefit in this system is that as the patient's information changes, the information on the card 1 can be changed immediately and easily. In one embodiment, the user will simply change the information by replacing the adhesive label 35 or writing/editing the information. In a second embodiment, the user will just edit the information in the computer system and print out a new card 1. This means the user's information can be current at all times as long as the user makes the changes as they occur. The user should make changes to any information that would have to be known by anyone attending to their care. This immediate information could make the difference between a life or death situation.

In these embodiments, in the event of an emergency, third parties can view the critical medical history of the user via the bandage 5 adhered to the user's body. In one embodiment, all of the information can be converted into a bar code 30 or QR code 32. The first responders will then either be able to use a general scanner to read the information or glean the information directly from the medical data card. This will also be beneficial to the hospitals because the hospitals can scan the patient's information into their computers. This will confirm whether the patient is a prior patient of the hospital or a new patient. They will be able to transfer the information upon arrival at the hospital onto the patient's hospital bracelet, saving precious time. The hospital employee will be able to scan each time from the bandage before each procedure, ie blood test, x-rays, ekg's, etc.

Further details of the computer-based system are described as follows. Persons of ordinary skill in the art understand that if the user has access to a computer or a computer tablet (or possibly a smart phone), these computer-related devices include a display screen and some type of keypad or user input interface. These computer-related devices employed by the user can communicate via tele-communications systems to a central computer which is often remote from the user's computer device. The central computer has a memory and various software programs which the user can access in order to produce the computer-generated medical data card described and shown earlier. The general steps for creating the medical data card are set forth earlier. The central computer has, typically, random access memory, permanent storage memory, a central processing unit and an input—output device. The input—output device is connected to the telecommunications network. The user's computer device also includes an input—output module which is connected to the telecommunications network. The user's device also includes a processor and typically includes random access memory and permanent storage memory. Programs are stored in the user's device typically as thin client programs. The central computer, during a set up operation, responds to an inquiry from the user's computer device. This response from the central computer includes an input web-based display screen, presented to the user, which the user completes for the user's personal profile (UPP). Once the UPP profile is created, and the user password is accepted by the central computer (the password being earlier input by the user), the central computer provides a list of medical conditions to the user. The user selects, typically from a menu format, any particular medical condition that the user experiences. Multiple menus in a menu tree format are provided in accordance with standard medical protocols and diagnosis. Once the user selects the appropriate medical diagnosis, the central computer then prompts the user to identify either specifics of the user (such as blood type) or types of medication associated with that diagnosis or special needs associated with that diagnosis (for example, auxiliary breathing apparatus if the patient has COPD). Once the user completes all this input into the central computer, the central computer generates data representing the medical data card. The central computer then outputs this data through the input—output module and the telecommunications network and sends it to the user's computer-related device, which user device accept as input data. The user's related device will have a printer attached to the computer-related device. The user's related device converts this digital data into a proper format to be printed by the user's printer. The user's computer-related device has an input—output module which delivers the digital data to the printer. The printer has a complimentary device which converts the digital data into printed format. Of course, the user may connect the user' computer-related device to the printer via a local network or Bluetooth™ network or wireless network. The user will be prompted by reminder emails, or other correspondence, to update their medical data card information. These reminders may be sent monthly or at any other appropriate time interval.

The claims appended hereto are meant to cover modifications and changes within the scope and spirit of the present invention.

What is claimed is:

1. A method of using a two-bandage system with a re-insertable medical data card comprising:
   providing a first bandage and a replacement bandage, both with a central pocket,
   each bandage having a slit for accessing said central pocket, a flap for sealing said central pocket, and a transparent faceplate on an outward facing surface of said central pocket, and an adhesive layer on an outer surface of a back of the bandage for adhering the bandage to the user;
   said medical data card containing pertinent medical data of a user;
   inserting into said central pocket of said first bandage said medical data card;
   placing said first bandage on the skin of the user thereby forming, in a first adhered condition, a wearable medical data card visible through said respective transparent faceplate;

after a period of three to four days, removing said first bandage from the skin, and removing said medical data card from the central pocket of said first bandage;

inserting said medical data card into the central pocket of said replacement bandage and placing the replacement bandage on the skin of the user, said replacement bandage thereby forming, in a second adhered condition, a second wearable medical data card visible through said respective transparent faceplate.

2. The method of claim 1, further comprising:

completing said medical data card with user supplied data displayed on adhesive backed labels onto the medical data card.

3. The method of claim 2, further comprising:

completing the medical data card with medical data supplied by the user by the user writing the medical data on the card.

4. The method of claim 1, further comprising displaying a computer readable code on said medical data card.

5. The method of claim 4, wherein the computer readable code is one of a bar code and a QR code.

6. The method of claim 1, providing said medical data card with the user's name, personal identifying information, blood type, allergies, medications, conditions, hospital and doctor of choice, person to be notified in event of emergency, and religion/faith.

7. The method of claim 1, wherein the medical data card is computer printed based upon user supplied medical data.

8. The method of claim 1, further comprising adhering an underside of said flap to create a substantially watertight seal on the central pocket.

9. The method of claim 1, further comprising displaying universal medical coding indicia on said medical data card, said universal medical coding indicia being one of a current procedural terminology and a local procedural terminology and a national procedural terminology.

10. The method of claim 1, wherein after said medical data card is removed from the central pocket of the first bandage, updating the pertinent medical data of the user; and re-inserting said medical data card into the central pocket of said replacement bandage.

* * * * *